United States Patent [19]

Adams

[11] Patent Number: 4,713,491

[45] Date of Patent: Dec. 15, 1987

[54] NINA'S BUTTERCUP-TIHITIAN SQUASH

[75] Inventor: Nina M. Adams, 16531 Eucalyptus Rd., Hesperia, Calif. 92345

[73] Assignee: Nina M. Adams, Hesperia, Calif.

[21] Appl. No.: 779,132

[22] Filed: Sep. 23, 1985

[51] Int. Cl.$^4$ ............................................. A01H 5/00

[52] U.S. Cl. ...................................................... 800/1

Primary Examiner—Robert E. Bagwill
Attorney, Agent, or Firm—Nina M. Adams

[57] ABSTRACT

A winter squash which keeps well and has firm, sweet, orange flesh.

2 Claims, No Drawings

NINA'S BUTTERCUP-TIHITIAN SQUASH

This invention relates to a new variety of winter squash. I planted a buttercup squash seed and discovered that the resulting fruit were nothing like those of buttercup squash. I planted seed and found that the new variety came true and did not revert to the buttercup squash. I have named my new variety Nina's Buttercup-Tihitian Squash.

BOTANICAL DESCRIPTION

Species: It has not been determined whether the new variety is a cross between *C. moschata* and *C. maxima,* or any other species cross.

Kind: Squash

Type: Winter

Plant: Long vine

Leaves: Medium in size, similar in texture to other winter squashes, shallow to deep-lobed, being dark green in color, with lighter greenish lines.

Flower: Deep yellow and of average size.

Fruit: The length can range from 18–24 inches, with the weight being from 7–20 lbs. The shape is similar to butternut or melon (Tahitian) squash. There are no ribs, the skin is smooth, and no warts are present.

Rind: The rind is thin, somewhat soft, green when immature but turning to gray gold in storage, being similar to melon (Tahitian) squash.

Flesh: The flesh is firm and fine in texture, moist, pale orange in color, with a sweet flavor, and excellent quality.

Seed cavity: The cavity is similar in size, shape, and location to butternut and melon (Tahitian) squashes.

Fruit stalk: The fruit stalk is about two inches in length, has a hard texture, is somewhat rough, and expanded at the attachment end.

Seeds: There are from 300 to 400 seeds per fruit. The seeds are about ½ inch long and ⅜ inch wide, having a smooth surface with a dull luster and a rounded margin. The color is near creamy-white.

The new variety is not particularly susceptible to the usual insects and diseases which attach squash plants.

The fruit of my new variety is similar in appearance to melon squash, in that they are both dark green when immature, ripening to a golden color. However, the flesh is similar to butternut squash in its rich flavor, but lacks the slight bitterness sometimes found in butternut squash.

I claim:

1. A new variety of winter squash known as Nina's Buttercup-Tihitian Squash.

2. Fruit of the squash variety of claim 1.

* * * * *